United States Patent
Ramamurthy

(10) Patent No.: US 8,691,390 B2
(45) Date of Patent: Apr. 8, 2014

(54) SINGLE-USE FLAMMABLE VAPOR SENSOR FILMS

(75) Inventor: Praveen C. Ramamurthy, Mansfield, OH (US)

(73) Assignee: Therm-O-Disc, Incorporated, Mansfield, OH (US)

( * ) Notice: Subject to any disclaimer, the term of this patent is extended or adjusted under 35 U.S.C. 154(b) by 1266 days.

(21) Appl. No.: 11/943,023

(22) Filed: Nov. 20, 2007

(65) Prior Publication Data
US 2009/0130421 A1 May 21, 2009

(51) Int. Cl.
B32B 3/14 (2006.01)
G01R 27/22 (2006.01)

(52) U.S. Cl.
USPC .......................................... 428/447; 324/691

(58) Field of Classification Search
USPC .................. 428/221, 447; 324/691
See application file for complete search history.

(56) References Cited

U.S. PATENT DOCUMENTS

| | | | |
|---|---|---|---|
| 3,045,198 A | 7/1962 | Dolan et al. |
| 3,234,180 A | 2/1966 | Wu |
| 3,539,530 A | 11/1970 | Karstedt |
| 3,699,073 A | 10/1972 | Wada et al. |
| 3,848,218 A | 11/1974 | Wakabayashi et al. |
| 3,864,659 A | 2/1975 | Furuuchi et al. |
| 3,974,122 A | 8/1976 | Sato et al. |
| 4,129,030 A | 12/1978 | Dolan |
| 4,224,595 A | 9/1980 | Dolan |
| 4,329,275 A | 5/1982 | Hatanaka et al. |
| 4,592,967 A | 6/1986 | Komatsu et al. |
| 4,621,249 A | 11/1986 | Uchikawa et al. |
| 4,631,952 A | 12/1986 | Donaghey |
| 4,673,910 A | 6/1987 | Uchikawa et al. |
| 4,686,524 A | 8/1987 | White |
| 4,691,186 A | 9/1987 | Shin et al. |
| 4,752,761 A | 6/1988 | Dolan et al. |
| 4,880,857 A | 11/1989 | Mori et al. |
| 4,921,976 A | 5/1990 | Kabeta |
| 4,938,860 A | 7/1990 | Wogoman |

(Continued)

FOREIGN PATENT DOCUMENTS

| AU | 2004201531 B2 | 12/2009 |
|---|---|---|
| AU | 2007201456 B2 | 3/2013 |

(Continued)

OTHER PUBLICATIONS

Silicon-Containing Monomers, Oligomers and Polymers as Sensitive Coatings for the Detection of Organic Solvent Vapors, Sensors and Actuators B 26-27 pp. 121-125, R Zhou et. al., (1995).*

(Continued)

*Primary Examiner* — Callie Shosho
*Assistant Examiner* — Kenneth Stachel
(74) *Attorney, Agent, or Firm* — Harness, Dickey & Pierce, P.L.C.

(57) ABSTRACT

A single-use replaceable (one-shot) conductometric sensor film for use with a conductometric sensor, such as flammable vapor sensors, is provided that detects one or more volatile organic compound chemical analytes. Such sensor films exhibit a sustained change in resistance after exposure to the target analytes. The sensor film compositions undergo substantially inelastic deformation after a detection event and thus exhibit a sustained resistance change, ensuring only one-time use for certain applications. Methods of sensing analytes using the single-use sensor film compositions are also provided.

17 Claims, 1 Drawing Sheet

(56) References Cited

U.S. PATENT DOCUMENTS

| | | | |
|---|---|---|---|
| 5,101,657 A * | 4/1992 | Lahlouh et al. | 73/40.5 R |
| 5,150,603 A | 9/1992 | Boenning et al. | |
| 5,169,909 A | 12/1992 | Okawa | |
| 5,256,574 A | 10/1993 | Neuburger et al. | |
| 5,283,308 A | 2/1994 | Bilgrien et al. | |
| 5,370,936 A | 12/1994 | Kaiya | |
| 5,418,136 A * | 5/1995 | Miller et al. | 435/5 |
| 5,512,882 A | 4/1996 | Stetter et al. | |
| 5,571,401 A | 11/1996 | Lewis et al. | |
| 5,593,787 A * | 1/1997 | Dauth et al. | 428/447 |
| 5,610,324 A | 3/1997 | Lawson | |
| 5,621,038 A | 4/1997 | Chen et al. | |
| 5,686,523 A | 11/1997 | Chen et al. | |
| 5,788,833 A | 8/1998 | Lewis et al. | |
| 5,789,485 A * | 8/1998 | Kobayashi et al. | 525/100 |
| 5,837,164 A | 11/1998 | Zhao | |
| 5,862,030 A | 1/1999 | Watkins, Jr. et al. | |
| 5,891,398 A | 4/1999 | Lewis et al. | |
| 5,911,872 A | 6/1999 | Lewis et al. | |
| 5,951,846 A | 9/1999 | Lewis et al. | |
| 5,959,191 A | 9/1999 | Lewis et al. | |
| 5,976,466 A | 11/1999 | Ratner et al. | |
| 5,979,227 A | 11/1999 | Lawson et al. | |
| 5,985,182 A | 11/1999 | Zhao | |
| 6,013,201 A | 1/2000 | Hayashida et al. | |
| 6,042,788 A | 3/2000 | De Wit et al. | |
| 6,074,576 A | 6/2000 | Zhao et al. | |
| 6,090,313 A | 7/2000 | Zhao | |
| 6,170,318 B1 * | 1/2001 | Lewis | 73/23.34 |
| 6,183,418 B1 | 2/2001 | Kuennecke | |
| 6,217,828 B1 | 4/2001 | Bretscher et al. | |
| 6,342,295 B1 | 1/2002 | Kobayashi | |
| 6,359,098 B1 | 3/2002 | Fehn et al. | |
| 6,375,821 B1 | 4/2002 | Jerome et al. | |
| 6,417,283 B1 | 7/2002 | Ikeda et al. | |
| 6,433,694 B1 | 8/2002 | Dolan et al. | |
| 6,444,323 B1 | 9/2002 | Matsumoto et al. | |
| 6,455,319 B1 | 9/2002 | Lewis et al. | |
| 6,518,371 B1 | 2/2003 | Fink et al. | |
| 6,710,123 B1 | 3/2004 | Amin-Sanayei et al. | |
| 6,740,701 B2 | 5/2004 | Chacko | |
| 6,815,520 B2 | 11/2004 | Yoneda et al. | |
| 6,840,069 B2 | 1/2005 | France et al. | |
| 6,868,350 B2 | 3/2005 | Zimmermann et al. | |
| 6,894,103 B2 | 5/2005 | Materne et al. | |
| 7,138,090 B2 | 11/2006 | Blok | |
| 7,171,312 B2 | 1/2007 | Steinthal et al. | |
| 7,211,637 B2 | 5/2007 | Blok | |
| 7,501,091 B2 | 3/2009 | Munoz et al. | |
| 7,645,422 B2 | 1/2010 | Blok et al. | |
| 7,708,947 B2 | 5/2010 | West et al. | |
| 8,012,420 B2 | 9/2011 | Ramamurthy et al. | |
| 2002/0161140 A1 | 10/2002 | Yoneda et al. | |
| 2003/0099574 A1 | 5/2003 | Bentsen et al. | |
| 2004/0202856 A1 * | 10/2004 | Blok | 428/325 |
| 2006/0292033 A1 * | 12/2006 | Blok et al. | 422/57 |
| 2007/0095678 A1 | 5/2007 | West et al. | |
| 2008/0025876 A1 | 1/2008 | Ramamurthy | |
| 2009/0130421 A1 | 5/2009 | Ramamurthy | |

FOREIGN PATENT DOCUMENTS

| | | |
|---|---|---|
| DE | 10029347 A1 | 1/2002 |
| EP | 0110371 A1 | 6/1984 |
| EP | 0232459 A1 | 8/1987 |
| EP | 0 363 006 A2 | 4/1990 |
| EP | 0 490 523 B1 | 6/1992 |
| EP | 0 434 396 B1 | 11/1994 |
| EP | 0 833 421 A2 | 4/1998 |
| EP | 1 088 849 A2 | 4/2001 |
| EP | 1 215 248 A2 | 6/2002 |
| EP | 1 254 924 | 11/2002 |
| EP | 1467199 A1 | 10/2004 |
| EP | 1019715 B1 | 1/2005 |
| EP | 1602691 A1 | 12/2005 |
| EP | 1895293 B1 | 11/2011 |
| JP | 62106358 | 5/1987 |
| JP | 02 309090 | 12/1990 |
| JP | 2311750 | 12/1990 |
| JP | 3073838 A | 3/1991 |
| JP | 4286949 A | 10/1992 |
| JP | 05 043823 | 2/1993 |
| JP | 07 258548 | 2/1993 |
| JP | 08 020725 | 1/1996 |
| JP | 08 120176 | 5/1996 |
| JP | 11 106657 | 4/1999 |
| JP | 2001124720 A | 5/2001 |
| JP | 2001 158856 | 6/2001 |
| JP | 2001165883 A | 6/2001 |
| JP | 2001 221225 | 8/2001 |
| JP | 2002-265787 A | 9/2002 |
| JP | 2003-121401 A | 4/2003 |
| JP | 2004510953 A | 4/2004 |
| RU | 1 582 597 A1 | 11/1995 |
| WO | WO 96/37547 | 11/1996 |
| WO | 9908105 A1 | 2/1999 |
| WO | WO 99/53300 | 10/1999 |
| WO | 0150117 A1 | 7/2001 |
| WO | WO 01/88042 A1 | 11/2001 |
| WO | WO 02/08314 | 1/2002 |
| WO | WO 02/23134 A1 | 3/2002 |
| WO | 02086911 A1 | 10/2002 |
| WO | 2004/107359 A1 | 12/2004 |

OTHER PUBLICATIONS

Lange's Handbook of Chemistry, Table 4.11 Sections titled Bond Dissociation Energies (1999).*
"Inco Special Products: Novamet and its Products: Nickel Oxides" [online], [retrieved on Sep. 21, 2005], retrieved from: www.incosp.com/novamet_products/nickel_oxides.
"Inco Special Products: Novamet Specialty Products" [online], [retrieved on Sep. 21, 2005], retrieved from: www.specon.com.au/Novamet.html.
"Carbon Black: Black Pearls 2000" [online], [retrieved on Aug. 28, 2006], retrieved from www.cabot-corp.com/cws/product.nsf/PDSDOCKEY/~~~BP2000?OpenDocument.
"Conductive Black: Vulcan XC72" [online], [retrieved on Aug. 28, 2006], retrieved from www.cabot-corp.com/cws/product.nsf/PDSKEY/~~~VXC72/$file/VULCAN_XC72-English.pdf?OpenElement.
"Inco Special Products: Inco Type 210 Extra Fine Nickel Powder" [online], [retrieved on Aug. 28, 2006], retrieved from www.incosp.com/products/type_210.
"SGL Carbon Group: Sigrafil C—continuous tow carbon fiber" [online], [retrieved on Aug. 28, 2006] retrieved from www.sglcarbon.com/sgl_t/fibers/pdf/sigrafil_c_e.pdf.
"Sigrafil C—the carbon fiber for industrial applications" [online], [retrieved on Aug. 28, 2006], retrieved from www.sglcarbon.de/sgl_t/fibers/sigra_c.html.
"Solutions for the Rubber Industry: Carbon Black Product Information" [online], [retrieved on Aug. 28, 2006], retrieved from www.degussa-fp.com/en/publikationen/produktinformationen/gummiru.Par.0029.pFile.tmp/E_PI_Printex_XE%202.pdf.
ASM International (Brinson, ed.), Engineered Materials Handbook, vol. 3, Adhesives and Sealants, (Dec. 1990), pp. 597-600.
Chen et al., "Electrochemical Synthesis of Polypyrrole Films Over Each of Well-Aligned Carbon Nanotubes," Synthetic Metals, vol. 125 (2002), pp. 289-294.
European Search Report for EP 04076097; Dated Jul. 30, 2004.
European Search Report for EP 05011207; Dated Sep. 1, 2005.
Ganter et al., "A New Generation of Addition Curing Silicone Heat Vulcanizing Rubbers," presented at Amer. Chem. Soc. Rubber Division, Cincinnati, OH, (Oct. 17-20, 2000), Paper 132.
Grate, J., "Solubility Properties of Siloxane Polymers for Chemical Sensors," Proceedings of SPIE-The International Society for Optical Engineering, vol. 2574 (1995), pp. 71-7.
Ho et al., "Review of Chemical Sensors for In-Situ Monitoring of Volatile Contaminants," SAND2001-0643, Mar. 2001.

(56) References Cited

OTHER PUBLICATIONS

Kim et al., "Electrical Properties of Conductive Polymers: Pet-Nanocomposites' Fibres," Autex Research Journal, vol. 4, No. 1 (2004), pp. 9-13.

Lewis et al., "Hydrosilylation Catalysts Derived from Cyclodextrin Organometallic Platinum Inclusion Compounds and Their Use in Command-Cure Applications," Journal of Inorganic and Organometallic Polymers, vol. 6, No. 2 (1996), pp. 123-144.

Lewis et al., "Platinum-Group Metal Cyclodextrin Complexes and Their Use as Command-Cure Catalysts in Silicones," Journal of Inorganic and Organometallic Polymers, vol. 5, No. 4 (1995), pp. 377-390.

Lewis et al., "The Chemistry of Fumarate and Maleate Inhibitors With Platinum Hydrosilylation Catalysts," Journal of Organometallic Chemistry, vol. 521 (1996), pp. 221-227.

Lin et al., "Percolated Network of Polystyrene Surface Grafted Multi-Walled Carbon Nanotubes in Polymer Thin Films," [online], [retrieved on Jul. 25, 2006], retrieved from: www.nanotubes.com.cn/papers/F-0-11-04.

March et al., Advanced Organic Chemistry; Reaction, Mechanisms, and Structures, 5th ed., Wiley & Sons, New York (2001), pp. 365-368.

March, Advanced Organic Chemistry; Reactions, Mechanisms, and Structures, 4th ed., Wiley & Sons, New York (c.1992), pp. 275-277.

Richner et al., "Grafted, Cross-Linked Carbon Black as a Double-Layer Capacitor Electrode Material," PSI Scientific Report, vol. V (2000), pp. 76-77.

Ronot et al., "Detection of Chemical Vapours with a Specifically Coated Optical-Fibre Sensor," Sensors and Actuators B, vol. 11 (1993), pp. 375-381.

Ronot et al., "Optimization and Performance of a Specifically Coated Intrinsic Optical-Fibre Sensor for the Detection of Alkane Compounds," Sensors and Actuators A, vol. 41-42 (1994), pp. 529-534.

Ronot-Trioli et al., "Solubility Interactions between Organic Vapors and Specific Polymeric Claddings for Optical Fiber Sensor," Sensors and Materials, vol. 7, No. 6 (1995) pp. 383-393.

Saruyama et al., "Development of New Hydrosilylation Cure System with Microencapsulated Platinum Catalysts"; presented at Amer. Chem. Soc. Rubber Division, Anaheim, CA, (May 6-9, 1997), Paper 64.

Schierbaum, "Application of Organic Supramolecular and Polymeric Compounds for Chemical Sensors," Sensors and Actuators B, vol. 18-19 (1994), pp. 71-76.

Hansen, George "High Aspect Ratio Sub-Micron and Nano-Scale Metal Filaments," Society for the Advancement of Material and Process Engineering Journal, vol. 41, No. 2, pp. 2-11 (Mar./Apr. 2005).

"Inco Type 210 Extra Fine Nickel Powder," Data Sheet, INCO Special Products (1999).

"Inco Type 210H Extra Fine Nickel Powder," Data Sheet, INCO Special Products (undated).

Lonergan, Mark C. et al., "Array-Based Vapor Sensing Using Chemically Sensitive, Carbon Black-Polymer Resistors," Chem. Mater., vol. 8, No. 9, pp. 2298-2312 (1996).

Sau, K.P. et al., "Electrical conductivity of carbon black and carbon fibre filled silicone rubber composites," Die Angewandte Makromolekulare Chemie, vol. 258, No. 1, pp. 11-17 (1998).

\* cited by examiner

SINGLE-USE FLAMMABLE VAPOR SENSOR FILMS

FIELD

The present disclosure relates to flammable vapor (FV) sensors, and more particularly to conductometric sensor films that detect vapor analytes.

BACKGROUND

The statements in this section merely provide background information related to the present disclosure and may not constitute prior art.

Detection of specific target analytes, or chemical compounds, is important for many applications, including for example, detecting whether the concentration of volatile organic analytes exceeds flammability limits. Various sensors available in the art utilize the physical changes in the sensor film to determine a concentration of analyte present, such as a conductometric sensor, or more particularly, a polymer-absorption chemiresistor sensor. A polymer-absorption chemiresistor has a polymer film sensor exposed to a surrounding atmosphere containing target analytes (chemical compounds). An electrical charge is applied across the polymer film. When the polymer absorbs target analytes, this results in a volumetric change of the film, and hence the electrical resistance of the film. In such films, conductive particles are generally distributed throughout the polymer film to enhance the sensitivity to resistance changes in the material when the volume of the polymer changes. Sensor films having good sensitivity to certain analytes and vast applicability for a variety of applications are desirable.

SUMMARY

In various aspects, the present disclosure provides a single-use conductometric sensor film for detecting one or more target analytes comprising volatile organic compounds, for example in a flammable vapor sensor. A replaceable sensor film matrix is in electrical communication with one or more electrodes of a conductometric sensor probe that detects one or more target analytes comprising volatile organic compounds. Where one or more target analytes are substantially absent, the matrix exhibits a first resistance. However, in the presence of one or more target analytes, the matrix exhibits a second resistance and further undergoes a substantially inelastic deformation to maintain a sustained resistance that is greater than the first resistance. The matrix comprises a crosslinked siloxane polymer and a plurality of conductive particles distributed within the polymer.

In certain aspects, the present disclosure provides methods of detecting one or more volatile organic compound target analytes. The method comprises monitoring an electrical potential of a single-use sensor film matrix having a baseline resistance. The sensor film matrix comprises a crosslinked siloxane polymer and a plurality of conductive particles. The method comprises detecting the presence of the target analytes by detecting a change in resistance over the baseline resistance of the sensor film matrix. Further, the sensor film matrix interacts with the target analytes to undergo a substantially inelastic deformation to result in a sustained increase in resistance.

In yet other aspects, the disclosure provides a single-use conductometric sensor film matrix comprising a crosslinked siloxane polymer and a plurality of conductive particles distributed within the polymer, where the polymer undergoes a substantially inelastic deformation in the presence of one or more target analytes comprising volatile organic compounds. Additionally, the crosslinked siloxane polymer exhibits a sustained change in resistance in the presence of one or more target analytes. The crosslinked siloxane polymer comprises a methacryloxy terminated siloxane precursor having a structure of:

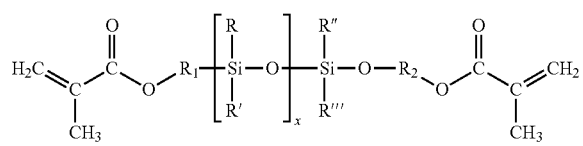

where each of R, R', R", and R''' are independently selected from a hydrocarbon side group, $R_1$ and $R_2$ are independently selected from an alkyl group; x ranges from about 65 to about 100 and has an average number molecular weight is about 650 to about 6,000.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way. The present disclosure will become more fully understood from the detailed description and the accompanying drawings, wherein.

DETAILED DESCRIPTION

Figure 1:
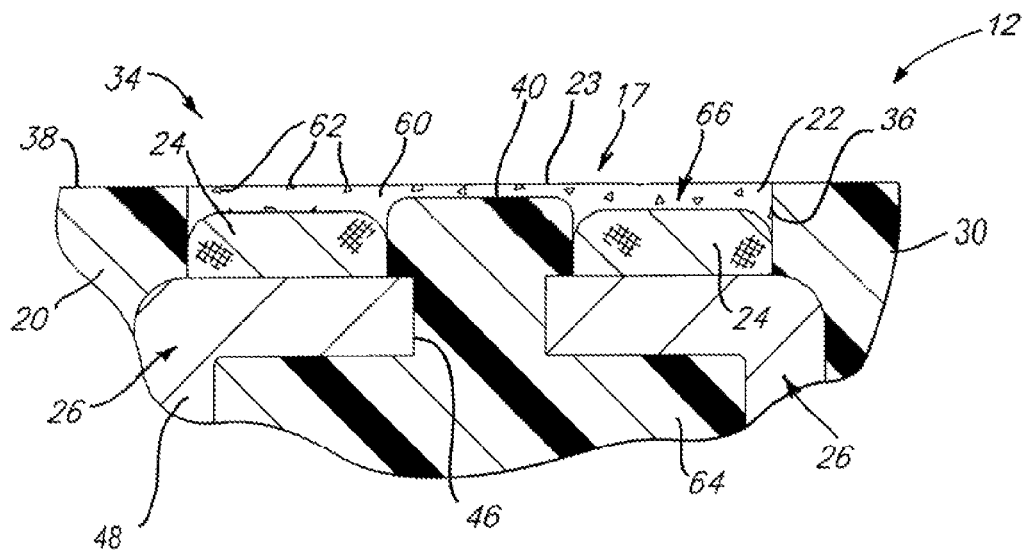
FIG. 1 is a detailed view of an exemplary conductometric sensor film.

The following description is merely exemplary in nature and is not intended to limit the present disclosure, application, or uses. It should be understood that throughout the drawings, corresponding reference numerals indicate like or corresponding parts and features.

Many of the materials currently employed as sensor films are selected for their sensitivity to certain target analyte compounds, which interact with the sensor film, often by absorption, adsorption, intercalation and the like. Many such polymeric materials have elastic and/or resilient properties (also referred to as "polymer memory recall") and are capable of elastic deformation, where such materials reversibly expand to a larger volume by interaction with target analytes and then return to an original contracted state post-deformation. In other words, most sensor film materials spring back or recover (e.g., contract) to an original state after removing the source of the physical stress. For example, such a physical stress is the physical presence of target analytes. As will be explained in more detail below, in accordance with the principles of the present disclosure, it is desirable to provide a sensor film which minimizes such elastic and/or resilient properties and which remains permanently deformed after exposure to target analytes. Thus, such sensor films are employed for a single application, i.e., a one-time use. The present disclosure provides a single-use conductometric sensor film that has superior sensitivity to desired volatile organic compounds (i.e., one or more target analytes), while being limited to a single use application in a conductometric sensor probe.

By way of background, FIG. 1 depicts a sensor film 22 of an exemplary conductometric sensor probe 12 that interacts with an external environment 17 to detect the presence of analytes, or target chemical compounds. In various aspects, the target analytes include one or more volatile organic compounds (VOCs). The sensor probe 12 generates an output signal based on continuous detection for analytes in the external environment 17, which is processed by a control unit (not shown).

A pair of electrodes 24 are optionally disposed beneath and attached to the sensor terminals 26. In lieu of electrodes, certain sensors have terminals 26 that protrude into the sensor film 22, and serve a similar function to the electrodes 24 (i.e., deliver current through the sensor film 22).

Terminals 26 are attached to the electrodes 24 and extend through both a first portion 30 and a second lower portion (not shown) of sensor probe 12. The electrodes 24 and terminals 26 are made of a conductive material, for example, a metal. The electrodes 24 each comprise a horizontal porous plate or mesh that is parallel to an external control surface 38. Each electrode 24 is connected to establish a conductive pathway to terminal 26. A first horizontal portion 46 of the terminal 26 makes either direct or indirect contact with the portion of the sensor film 22 seated within apertures 36 to detect changes in the resistance of the sensor film 22. Extending from the first horizontal portion 46 is a first vertical portion 48. The terminals 26 connect to external or end lead terminals (not shown).

The conductometric sensor film 22 comprises a polymer 60 with a plurality of conductive particles 62 dispersed therein. In certain aspects, the sensor film 22 includes conductive particles 62 distributed homogeneously or evenly throughout the polymer 60 thereby forming a sensor film 22 that is a conductive polymeric matrix 66. "Matrix" refers generally to a polymer system with filler particles distributed therethrough. The terminals 26 extend through a body 64 of the sensor probe housing 20 and are electrically connected to the electrodes 24. The electrodes 24 protrude into the sensing region 34 and into the sensor film 22. Thus, the electrodes 24 and terminals 26 are in electrical communication with the sensor film 22. In certain aspects, the electrodes 24 are situated near the external control surface 38 and further across the sensor film 22, for even current distribution.

In the exemplary conductometric sensor film shown, the conductive sensor film matrix 66 is seated upon the control surface 38 such that the matrix 66 fills the apertures 36 and spans a center control surface 40. The matrix 66 fills the apertures 36 so that the matrix 66 is in either direct or indirect electrical contact with both of the electrodes 24. Upon exposure of the sensor matrix 66 to target analytes, the matrix 66 volume typically increases by swelling.

The polymer 60 of the sensor film 22 is a polymer that readily absorbs a target analyte or chemical compound, through a gas-solid interface occurring between a surface 23 of the sensor film 22 and the surrounding gas in the external environment 17 at a rate that is relatively proportional to the concentration of the analyte in the surrounding gas. Thus, a correlation can be made between the quantity of analyte absorbed, and the concentration of the analyte in the surrounding gas. In the exemplary sensor probe 12 depicted, the change in the volume of the sensor film 22 is correlated to the concentration of the analyte present in the gas and is further related to the electrical resistance of the sensor film 22.

Of particular interest are sensor films 22 that detect vaporous hydrocarbon compounds, such as volatile organic compounds (VOCs). Thus, in the substantial absence of target analytes, the sensor film 22 exhibits a baseline resistance. By "substantial absence" it is meant that the concentration of target analytes is below a predetermined threshold concentration, as it is possible that compounds may be present in the atmosphere in amounts below detection limits or below lower flammability limits, for example. In the presence of target analytes above a specific concentration, the resistance of the sensor film 22 increases to a level detectable by the sensor probe 12. Compatible polymers for detecting VOCs include siloxane polymers. A variety of siloxane based polymers are contemplated in the present disclosure, and further discussed below.

Figure 2:
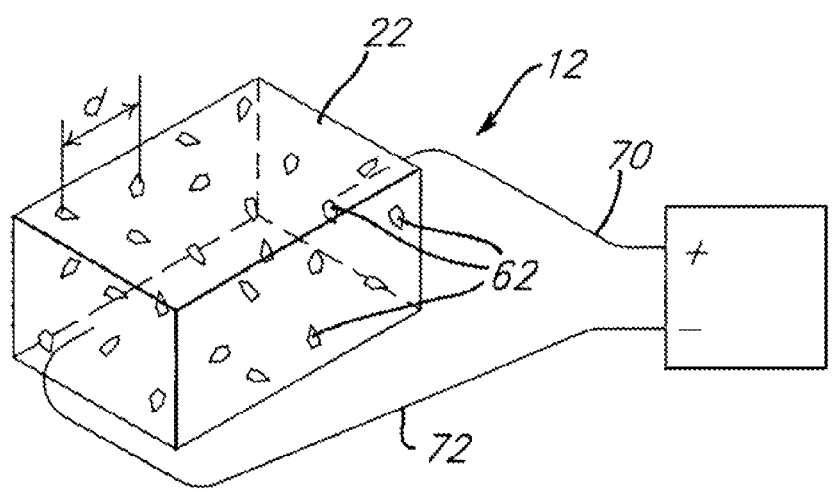
FIG. 2 is a schematic illustration of operating principles of a matrix polymer film of a polymer absorption chemiresistor.

As shown in FIG. 2, the operational principle of a polymer-absorption chemiresistor sensor probe 12 involves applying a current through the sensor film 22 between a positive 70 and a negative lead 72. The positive and negative leads 70, 72 are optionally electrodes, such as those shown at 24 in FIG. 1. Conductive particles 62 are distributed throughout the sensor film 22 to enhance the electrical conductivity of the matrix 66. Resistance measurements are taken across the sensor film 22 via monitoring of the current and potential difference across the sensor film 22 between the negative and positive leads 70, 72, and typically is measured by the processing or control unit 14 (not shown) attached to the sensor probe 12.

Resistance values vary with the distance "d" between the conductive particles. Initially, prior to exposure to target analytes, the matrix 66 has a first baseline resistance. As the distance "d" between the conductive particles 62 increases, the resistance proportionally changes over the baseline resistance, as well. In various aspects, the resistance of the sensor film 22 increases when the distance between conductive particles 62 increases. Thus, any increase in the volume of the sensor film 22 affects the overall resistance measurements. Upon detection of a change in resistance between the positive and negative leads 70, 72 the sensor provides a signal indicating the presence of the substance for which the sensor film 22 has an affinity. Consequently, the change in resistance of the sensor film 22 detected by the electrodes 70, 72 once the resistance reaches a second resistance indicates the presence of the target analyte.

Generally, the sensor film 22 has an initial physical state, for example, an initial volume prior to exposure to target analytes. When the sensor film 22 volume increases in the presence of one or more target analytes, the first state begins to deform (e.g., to expand). It should be noted that while the present disclosure describes expansion or increased volume of the sensor film 22 when the film is exposed to analytes, some suitable sensor film materials may behave differently in the presence of such analytes and the disclosure is not limited solely to expansion, but also encompasses contraction or other mechanisms by which the sensor film's physical characteristics change in a detectable manner. A typical sensor film, including a crosslinked polymer, undergoes reversible deformation from the first physical state (e.g., occupying a first volume) to a second physical state (e.g., occupying a second volume). In a typical conductometric sensor film 22, where the distance "d" decreases when target analytes are removed, the resistance also decreases. In other words, when the concentration of analytes in the surrounding environment 17 falls or such analytes are subsequently removed from the environment 17 (and consequently from the sensor film 22), then the polymer and hence a conventional sensor film matrix 22 reverts back to its original physical state due to elastic deformation and thus to a similar baseline resistance.

However, in certain applications, it is desirable for sensor films to have properties that restrict use of such a film after single use or a detection event that senses one or more target analytes. As used herein, when one or more target analytes are present above a threshold concentration or a predetermined level the sensor film exhibits a change in resistance, referred to herein as "detection event." Such single-use applications may be particularly useful to ensure appropriate sensor readings and accuracy of the sensor probe without requiring intermittent calibration of the sensor control unit after a detection event or extensive equipment costs to enhance safety of flammable vapor sensors, for example in consumer products.

In certain applications, replaceable or disposable sensor films are intended for use in a single application and thus are discarded and replaced after a detection event with a new replacement sensor film. Often, in such applications, the sensor controller is programmed to be reset after a detection event, when the used or spent sensor film is replaced with a new sensor film. However, sensor controls may potentially be overridden or reprogrammed to force a reset, without replacing the spent sensor film with a replacement sensor film. In the case of traditional sensor film materials, the baseline resistance may change slightly after exposure to analytes, however the sensor controller and other equipment are frequently calibrated to account for such changes. Hence, in more complex sensor systems, the sensor can be recalibrated to account for any changes in the sensor film, where accuracy of the readings is verified as necessary. However, for certain less complex sensor applications, such as single-use sensor systems, the sensor is designed to monitor a standard baseline resistance value (or a baseline resistance value that falls within a predetermined range) and is ideally replaced with a new replacement sensor film prior to reset for subsequent monitoring and operation.

Thus, in various aspects, sensor films according to the present disclosure provide an additional measure of safety in such single-use sensor systems, ensuring that single-use sensor films are only used once and discarded after a detection event. Such sensor films are substantially irreversibly deformed upon exposure to analytes. By "substantially" it is meant that the polymer exhibits the stated property or undergoes the stated action to the extent that the desired effect or result is achieved. For example, where a polymer undergoes substantially irreversible deformation, the deformation after exposure to analytes leads to a desired effect of the sensor film matrix having a sustained change in resistance, even though some of the polymer matrix may experience some elastic deformation, rather than solely irreversible plastic deformation, as will be described in more detail below. However, the level of substantially irreversible deformation in the polymer is sufficient to provide the increase in resistance that minimizes and/or prevents potential reuse of the single-use sensor film. In this manner, such sensor films provide both accurate sensor detection and prevent accidental re-use of a spent disposable sensor film after a detection event, thus improving sensor accuracy and safety.

In various embodiments, the sensor film 22 comprises a crosslinked polymer resin. As used herein, the term "polymer" encompasses homopolymers and copolymers. The term "copolymer" generically refers to a polymeric structure that has two or more monomers polymerized with one another, and includes polymers such as terpolymers with three combined monomers. A "homopolymer" refers to a polymer formed of a single repeating monomer. In various aspects, the polymer is formed from the reaction between at least two precursor moieties or polymers having reactive functional groups that undergo crosslinking. A polymer precursor includes any monomer, polymer, or copolymer having at least one functional group for crosslinking that is incorporated into the crosslinked polymer.

In various embodiments, the polymer comprises siloxane or a so-called silicone polymer. A "siloxane polymer" as used herein, refers to a cross-linked polymer that has a basic backbone of silicon and oxygen with side constituent groups that may be the same or different, generally described by the structural repeating unit $(\text{—O—SiRR'—})_n$, where R and R' may be the same or different side constituent groups, and n may be any value above 2 designating the repetition of the SRU in the polymer backbone. Siloxane polymers may include polyheterosiloxanes, where side groups and/or structural repeating units may be different entities (having different side constituent groups), such as, for example, the siloxane co-polymer described by the nominal SRU formula, $(\text{—O—SiRR'})_n\text{—}(\text{—O—Si—R"R'"})_m$, wherein R and R' are distinct side groups from R" and R'". Further R and R' may be different from one another, likewise the same may be true for R" and R'". Furthermore, such side groups may be referred to as "branched" indicating side groups attached to the siloxane backbone. Such siloxane polymers may terminate in any variety of terminal groups, such as for example, trimethyl silyl ($(CH_3)_3Si$) terminated siloxane, or ethyl vinyl terminated siloxane, which will be described in more detail below.

Siloxane polymers can be formed by various reaction mechanisms, which are divided generally into two classes: solvent borne (solvent dispersions of high molecular weight solids) and room-temperature vulcanizing (RTV). RTV materials are usually further divided into RTV-I and RTV-II categories. RTV-I is a siloxane curing system that cures upon exposure to water and is typically a one-part system. An RTV-II system is typically a two-component formulation that is generally capable of curing at room temperature when all the components are mixed. RTV-II is known as an addition-curing (or addition-crosslinking) mechanism. In addition-cure systems, siloxane materials typically crosslink by reaction of an aliphatically unsaturated functional group in a polymer precursor or moiety with Si-bonded hydrogen functional groups in a second polymer precursor via a hydrosilylation reaction in the presence of a catalyst, typically a platinum-containing compound. Addition-cure siloxane materials have generally been prepared as two-component formulations, which separate the respective polymer precursors having the silicon hydride crosslinking functional groups (SiH) from the polymer precursor reactant materials having aliphatically unsaturated functional groups, to permit control over when the formation of the crosslinked siloxane product occurs.

In certain aspects of the present disclosure, the sensor film 22 comprises a crosslinked siloxane polymer base, where the siloxane polymer backbone has at least one moiety with a large hydrocarbon substituted side group represented by R' in the nominal general formula for the structural repeating unit $(\text{—O—SiRR'})_n$. A "hydrocarbon side group," as used herein, includes any hydrocarbon or hydrocarbon derived side group with at least one carbon atom or greater. Examples of such hydrocarbon side groups include: alkyl and aryl groups greater than a methyl group, optionally greater than an ethyl group, branched alkyl groups, aromatics, modified hydrocarbon compounds comprising a polar groups, or mixtures thereof. Polar group modified hydrocarbons incorporate a polar molecule or molecular group into the hydrocarbon side group structure, with the effect of imparting polarity on the entire side group. Such polar atoms or groups may include, for example, oxygen, nitrogen, or ammonia, cyano or hydroxyl groups. Examples of suitable hydrocarbon side groups include without limitation: methyl, ethyl, propyl, butyl, pentyl, hexyl, heptyl, octyl, nonyl, decyl, phenyl, alkylphenyl, cyclopentyl, and phenylpropyl. In certain aspects, select hydrocarbon side groups optionally comprise alkyl groups with eight or more carbon atoms (octyl groups or higher) to enhance temperature stability and detection of certain VOC analytes, as described in U.S. Pat. No. 7,138,090 to Blok, which is commonly assigned to the present assignee, the content of which is incorporated by reference in its entirety. Other hydrocarbon side groups comprising a polar group include, for example, butylated aryloxypropyl, N-pyrrolidonepropyl, cyanopropyl, benzyltrimethyl ammonium chloride and hydroxyalkyl.

In various aspects of the disclosure, the crosslinked siloxane polymer that is selected for use in the sensor film has certain desirable physical properties that relate to a single-use sensor film. The present disclosure provides a single-use conductometric sensor film comprising a matrix that includes a crosslinked siloxane polymer and a plurality of conductive particles that are distributed within the polymer. The polymer of the present teachings undergoes a substantially inelastic deformation in the presence of one or more target analytes comprising volatile organic compounds and exhibits a sustained change in resistance. Elastic deformation generally refers to deformation that is nonpermanent and is recovered upon release of an applied stress. By inelastic deformation, it is meant that the polymer undergoes substantially permanent, non-recoverable plastic deformation with the application of an applied stress above a specific threshold, for example, above a yield strength ($\sigma_y$) of the material. Thus, the polymer material deformation transforms from elastic to plastic under applied stress. In other words, a polymer has a first state and after absorption or interaction with the volatile organic target analyte(s) (i.e., an applied stress), the polymer is substantially deformed in an irreversible manner to a second state, and thus is incapable of reverting back to its original, first state. In various aspects of the present teachings, this substantially inelastic deformation is achieved by one of several mechanisms that will be described in more detail below.

By a "sustained" high resistance, it is meant that even after the concentration of target analytes is significantly reduced to below detection levels by the sensor film, the applied potential to the sensor film results in a resistance level that does not proportionally reduce with the reduction in analyte concentration. In certain aspects, a base resistance exhibited by the sensor film matrix prior to the exposure to one or more target analytes at ambient temperature and pressure conditions is less than or equal to about 100 Ohm, optionally less than or equal to about 50 Ohm, optionally less than or equal to about 40 Ohm, and in certain embodiments less than or equal to about 20 Ohm.

"About" when applied to values indicates that the calculation or the measurement allows some slight imprecision in the value (with some approach to exactness in the value; approximately or reasonably close to the value; nearly). If, for some reason, the imprecision provided by "about" is not otherwise understood in the art with this ordinary meaning, then "about" as used herein indicates a possible variation of up to 5% in the value.

In some embodiments, the sensor has a base resistance of less than or equal to about 10 Ohm. Where one or more target analytes are present, the increase in resistance (sustained resistance) over the baseline resistance is at least about a 100% increase, for example increasing to greater than or equal to about 300,000 Ohm, optionally greater than or equal to about 400,000 Ohm, and optionally greater than or equal to about 800,000 Ohm. A sustained resistance increase maintains a sensor film matrix resistance at a relatively high level, which may be less than a peak resistance in the presence of target analytes, but is significantly greater than a baseline resistance of the sensor film matrix. By way of non-limiting example, the sustained resistance is at least about 100% greater than a baseline resistance, optionally about 200% greater than a baseline resistance; optionally about 400% greater than a baseline resistance.

The substantially inelastic deformation of the crosslinked siloxane polymer of the sensor film matrix can be achieved by a first mechanism, a second mechanism, or a combination of the first and second mechanisms. First, in accordance with the principles of the present disclosure, a crosslinked siloxane polymer optionally has a relatively loose physical network meaning that there is a relatively low amount of branching (a relatively greater proportion of longer chains in the network and/or a lower density of crosslinking points between the respective precursor components that form the crosslinked polymer network). Such a loose polymer network ensures that after deformation, resulting from the matrix interaction and/or absorption of one or more volatile organic compounds, the loose: polymer network in the matrix lacks the crosslinking density and branching necessary for sufficient elasticity to enable the polymer network to return to the original state macroscopically (i.e., it lacks recoverability). The loose polymer network can be achieved in accordance with the present teachings by incorporating a relatively large quantity of polymer precursors into the crosslinked siloxane polymer that have terminal functional groups (rather than mid-chain functional groups) for the crosslinking reactions that form the crosslinked siloxane polymer. Such a relatively high proportion of terminal functional groups lowers the density of crosslinking points and increases the relative length and/or linearity of the polymer network, while maintaining sufficient physical properties of the polymer to be capable of detecting/interacting with the volatile organic target analytes. In certain aspects, the polymer matrix has a first initial volume prior to exposure to the target analytes and a second expanded volume after exposure to the target analytes. The polymer matrix has the second expanded volume even after the target analytes are removed or absent. The sensor film 22 thus has a sustained increase in resistance when a volatile organic compound analyte is detected and it is believed that due to the substantially inelastic deformation, the sensor film resistance does not change significantly after the detection event because the polymer remains at the second expanded volume.

Polymer precursors having terminal reactive groups include moieties having at least one terminal group at the end of various siloxane chains. Suitable terminal reactive groups include vinyl and/or hydride groups. As described above, the presence of such terminal groups reduces the amount of crosslinking points within the crosslinked siloxane polymer network, thus providing a physical network having a lower crosslinking point density and consequently a relatively loose polymer network having a reduced elasticity. In various aspects, where the crosslinked siloxane polymer has a loose network structure, the crosslinked polymer comprises at least about 50% by weight of a polymer precursor having terminal functional groups. In certain aspects, the crosslinked siloxane polymer comprises at least about 60%; optionally at least about 70%; optionally at least about 80%, optionally at least about optionally at least about 90% of the polymer precursor having terminal functional groups. In certain aspects about 50 to about 80% of the crosslinked siloxane polymer comprises a polymer precursor having terminal functional groups.

The present disclosure also provides a second mechanism by which a siloxane polymer of the sensor film is designed to have the substantially inelastic deformation. At least one polymer precursor is selected to have a weak bond that will break upon physical deformation of the polymer network in a localized region near the weak bond. For example, where the sensor film expands in volume in the presence of one or more volatile organic target analytes, the weak bonds or fragile points in the crosslinked siloxane polymer break or cleave. Where the volume increases in the presence of target analytes, the polymer remains at this increased volume and due to fracturing and/or breakage and cannot elastically recover and contract back to an initial volume. Thus, the physical change in the sensor film matrix 22 is sustained so that it exhibits a sustained resistance change. As such, the sensor having so-called fragile points or weak bonds provides for a single use sensor film that desirably necessitates replacement of a spent sensor film with a new sensor film after a detection event.

By a "weak bond" it is meant that at least one bond within the crosslinked siloxane polymer has a weak bond strength in comparison to other bonds in the polymer. Such a weak bond strength can be expressed by several different metrics known to those of skill in the art. One exemplary means to determine a weak bond is by a bond dissociation energy, which is generally defined as the measure of the strength of a particular chemical bond and is usually expressed as the standard enthalpy change when a bond breaks, for example, when a bond (A-B) is cleaved by a reaction at room temperature (298 K) (to form A and B). The bond dissociation energy is often expressed as $D°_{298}$, which as recognized by those of skill in the art, is often difficult to measure and quantify in polyatomic molecules, since the mechanisms of the kinetic systems involved are often complex and significant disparities in data are frequently observed. Thus, the bond dissociation energies as set forth below are based on current knowledge in the art, however may be further refined in the future. In various aspects, a weak bond has an average bond dissociation energy of less than or equal to about 295 kJ/mol; optionally less than or equal to about 290 kJ/mol; optionally less than or equal to about 280 kJ/mol. In certain aspects, the weak bond has an average bond dissociation of less than or equal to about 250 kJ/mol, optionally less than or equal to about 200 kJ/mol. By way of example, the bond dissociation energy for an Si—O bond is estimated to be about 788 kJ/mol where the polyatomic molecular effects are neglected, the Si—H bond is about 298.5 KJ/mol, the Si—C bond is about 435 kJ/mol, the C—C bond is about 607 kJ/mol, the C—H bond is about 337 kJ/mol, and the C=O carbonyl is about 750 kJ/mol, pursuant to those values set forth in Lange's Handbook of Chemistry, $14^{th}$ ed., in Table 4.11, pp. 4.25 to 4.35 (1992), which is incorporated by reference. Similarly, the CRC Handbook of Chemistry and Physic, $86^{th}$ ed., Ch. 9, pp. 9-54 to 9-76 (2005-2006), sets forth Bond Dissociation Energies in Diatomic Molecules (Table 1), Bond Dissociation Energies in Polyatomic Molecules (Table 3), and Enthalpies of Formation of Free Radicals and Other Transient Species (Table 4), which is incorporated by reference. In certain aspects, a single-use conductometric sensor film has a crosslinked siloxane polymer that comprises at least one bond with a weak bond strength and a bond dissociation energy of less than or equal to about 295 kJ/mol.

For example, in certain aspects, a crosslinked siloxane polymer of the present teachings is formed with a polymer precursor that is a methacryloxy copolymer precursor having a vinyl group for crosslinking, which results in methacryl bonds in the crosslinked polymer, which are believed to break upon physical deformation of the surrounding polymer network. While not limiting the present teachings to any particular theory, it is believed that the weak bond in a methacryl group is the ester bond between the carbonyl group (C=O) and an adjacent carbon. This ester bond is believed to have the lowest bond dissociation energy, relative to the bond dissociation energies of the siloxane backbone (Si—O bonds), the silicon-carbon bonds (e.g., Si—R or Si—R'), the hydrocarbon bonds (e.g., within R or R'), and the carbonyl groups of the final crosslinked siloxane polymer.

In one aspect, the crosslinked polymer is formed by a first polymer precursor comprising methacryloxy and hence a vinyl group and a second polymer precursor having terminal hydride functional groups. The methacryl bonds in the crosslinked polymer have a weak bond strength. In certain aspects, a ratio of the first polymer precursor to the second polymer precursor is about 1:10 to about 1:1 by weight.

In certain aspects, the crosslinked siloxane polymer is formed by employing a polymer precursor that includes both a weak bond and a terminal functional group, thus providing both the fragile network points and a loose polymer network. Such a polymer precursor is represented below, where R, R', R", and R'" are selected as described above in the context of a general siloxane polymer discussion (from various hydrocarbon groups), and where $R_1$ and $R_2$ are likewise independently selected from alkyl hydrocarbon groups, such as methyl, ethyl, propyl, butyl, pentyl, hexyl, heptyl, octyl, nonyl, decyl, and the like.

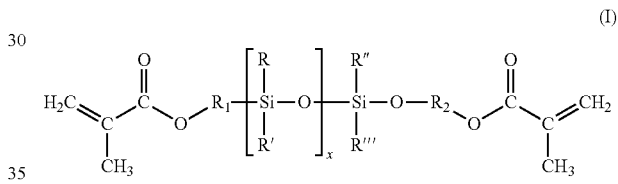

(I)

x optionally ranges from 65 to about 100 and an average number molecular weight is about 650 to about 6,000. The average number molecular weight is obtained by dividing the chains of polymer into a series of size ranges and then determining the number fraction of chains with each size range, expressed as $\overline{M}_n = \Sigma x_i M_i$, where $M_i$ represents the mean molecular weight of size range i, and $x_i$ is the fraction of the total number of chains within the corresponding size range.

For example, in certain aspects, a particularly suitable methacryloxy terminated siloxane precursor of the present disclosure has a structure of:

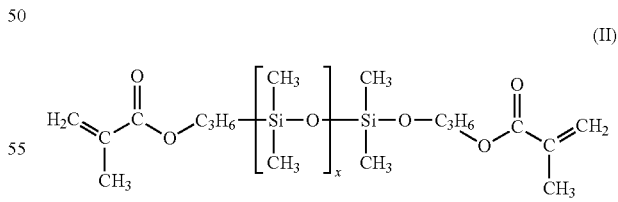

(II)

where x ranges from about 65 to about 100, R, R', R", and R'" are all selected to be methyl and $R_1$ and $R_2$ are $C_3H_6$ (propyl). The methacryl group has vinyl functional groups at a terminus of the respective polymer precursor chains, as well as a weak bond in the oxygen bonded in the ester to both the propyl group ($C_3H_6$) and the carbonyl group (C=O). In certain aspects, such a polymer precursor has an average number molecular weight of about 650 to about 6,000. In certain aspects, the crosslinked siloxane polymer has a precursor according to the Structure II above, where x equals 65 and the average number molecular weight is about 5,000.

Aside from the moiety of the polymer precursor having the weak bond and/or the terminal functional groups, the crosslinked siloxane optionally comprises other precursor siloxane polymers, such as those optionally having R, R', R", and R'", selected to be a large hydrocarbon side group, such as an octyl hydrocarbon side group that forms an octylmethylsiloxane monomer. One example of a suitable siloxane precursor having a copolymer (e.g., terpolymer) structure with a vinyl functional group is poly(vinylmethylsiloxane-octylmethylsiloxane-dimethylsiloxane). Exemplary ranges of the quantity of monomers in such a terpolymer include (3-5% vinylmethylsiloxane)-(35-75% octylmethysiloxane)-(20%-62% dimethylsiloxane), where one monomer is represented by (—O—SiRR'—), where R is methyl and R' is selected to be an octyl side group, incorporated into the siloxane monomer. Another example of a suitable siloxane polymer precursor is a polyphenylmethylsiloxane, where the phenyl is the large hydrocarbon side group and the polymer has vinyl terminal groups for subsequent crosslinking.

In various aspects, as described above, the crosslinked siloxane polymer is formed by a crosslinking reaction between the first siloxane precursor having a vinyl group and a second siloxane precursor having a hydride group, in the presence of a catalyst. For example, one suitable polymer precursor having a hydride group comprises (7-13% hydromethylsiloxane)-(87-93% octylmethylsiloxane), which has an average molecular weight of about 6000, and is capable of crosslinking with the first polymer precursors described above having vinyl groups.

The crosslinking reaction may be carried out by conventional means, such as by exposure to irradiation or peroxide, moisture cure by a condensation reaction, or a hydrosilylation reaction in the presence of a catalyst. Any method of crosslinking siloxane polymers may be used, as recognized by one of skill in the art. In certain aspects, crosslinking is achieved by a hydrosilylation reaction in the presence of a catalyst, which can generally be conducted at lower temperatures and where the control over the degree of crosslinking is greater.

Crosslinking by hydrosilylation generally employs a catalyst and a crosslinking (curing) reagent which reacts with accessible functional groups on at least some of the side groups within the siloxane polymer. A siloxane polymer precursor or silane containing hydride functional groups, such as those described above, are frequently referred to as a crosslinking/curing reagent in an addition-cure hydrosilylation reaction. An example of a suitable hydrosilylation crosslinking reaction includes, for example, a methacryloxy terminated siloxane precursor (having vinyl functional groups) reacted with a hydride containing siloxane precursor (or crosslinking reagent) polymethylhydrosiloxane octylmethylhydrosiloxane copolymer, where the vinyl and hydride groups react in the presence of a platinum catalyst to result in a crosslinked siloxane polymer. Polymethylhydrosiloxane-octylmethylhydrosiloxane copolymer is commercially available as the product HAM 301, from Gelest, Inc. of Tullytown, Pa. The hydrosilylation reaction facilitates crosslinking between neighboring siloxane chains at the functional group sites which create crosslinking points.

Other feasible catalyst systems that may be used for hydrosilylation (in addition to platinum) in the present disclosure include, for example: platinum carbonyl cyclovinylmethysiloxane complex used for elevated cures, such as SIP 6829 which is also commercially available from Gelest, Inc.; Rh(I) catalysts such as $(PPh_3)_3RhCl$ or $[(C_2H_4)_2RhCl]_2$, Ni catalysts, $(PPh_3)PdCl_2$, $Rh_2(OAc)_4$, $Ru_3(CO)_{12}$, and $Co_2(CO)_8$ and equivalents thereof. While the crosslinked siloxane polymer optionally is formed from one or more polymer precursors having at least one terminal functional group, other precursor compounds may have functional groups present along the siloxane backbone or also at the chain ends to allow for subsequent crosslinking. The functional groups within the polymer precursors may be distributed randomly or may be regularly ordered within the polymer precursor.

In certain aspects, the crosslinking reaction is achieved through a hydrosilylation reaction by adding at least one polymer precursor having a vinyl group, at least one polymer precursor having a hydride group (e.g., a curing reagent), and a catalyst. The rate of reaction for crosslinking is related to temperature and is accelerated when temperature is raised; a catalyst is added; or both. Temperature may be used to control the rate of reaction to coincide with processing needs. Further, the addition of the catalyst may be prolonged until the mixture is ready to be processed for application onto the sensor. In certain aspects, the curing reagent is added in the range of about 1 to about 5 weight % of the total crosslinked siloxane (including all other polymer precursors). In certain aspects, catalyst is charged to the polymer precursor mixture at about 0.05 to about 1 weight percent of the total polymer mixture (excluding conductive particles).

A matrix mixture may be formed by admixing a plurality of conductive particles into the polymer resin (where there is more than a single species, the conductive particles are premixed prior to charging with the catalyst). The plurality of conductive particles are added in a range of about 25 to about 75% of the total mixture depending on particle characteristics, including tendency to disperse in the matrix. Suitable conductive particles include those recognized by one of skill in the art, such as, for example, gold, platinum, graphite (i.e., hexagonally crystallized carbon), carbon black, nickel, silver, conductive metal borides, nitrides or carbides. In certain aspects, the conductive particles comprise carbon black. In certain aspects, conductive particles are selected from large particle size carbon black conductive particles with an $N_2$ adsorption value of less than 25 and DBP absorption of less than about 180 ml/100 g. Examples of commercially available conductive carbon black particles that fulfill the preferred physical characteristic ranges above include: Asahi 15HS or AS N880, both manufactured by Asahi Carbon Co., Ltd. of Japan; or CC N880 from Cancarb Ltd. of Alberta, Canada; and Spheron® 5000 or Spheron® 6000 both available from the Cabot Corporation of Boston, Mass. Suitable ranges of the mean particle size are about 90 to about 400 nanometers.

The amount of conductive particles added is dependent on the individual characteristics of the particle selected, but can be about 25 to about 75 percent by weight of the total mixture. In certain aspects, the plurality of conductive particles is well mixed into the polymer mixture for even distribution. The polymer or matrix mixture can be blended or mixed by equipment known in the art, such as for example, a mixer (e.g., a Banbury® or Brabender® mixer), a kneader, a monoaxial or biaxial extruder (e.g., single-screw or twin-screw extruders).

The handling and flowability of a matrix mixture is generally related to the rate of crosslinking after the catalyst is added, which affects the viscosity of the mixture. The amount of time that remains for handling is generally known as the "pot life," and may range from many hours at room temperature to less than an hour if temperatures are sufficient, as known to those of skill in the art. The crosslinking or curing reaction may be prolonged by addition of inhibitors, which are well known in the art, as a means for retarding the reaction. The crosslinking or curing reaction can be performed entirely at room temperature, or may be accelerated by heating the mixture, depending on the processing needs. Suitable curing temperatures range from about 30° C. to about 250° C.

The matrix mixture is then applied to the probe sensor surface by conventional application means (e.g., doctor blade, casting, lamination, extrusion, pad printing, spraying or silk screening). After application, further sensor components and processing may be completed, such as applying a protective cap. In other aspects, the sensor film matrix may be pre-formed in molds and the like to form sensor film inserts or disposable replacement cartridges that can be arranged in electrical communication or contact with electrodes and other appropriate regions of the sensor surface. In certain aspects, the entire conductometric probe may be replaceable. Curing, as discussed above, occurs by any method known by those of skill in the art, such as by placing the sensor with a matrix mixture applied into an oven at elevated temperature, for example, for 3 to 8 hours at 120° C. to 130° C. However, many variations of curing the siloxane polymer in the matrix mixture are feasible with the present disclosure.

Details regarding the preparation of certain embodiments of the present disclosure will now be described in detail.

EXAMPLE 1

A single-use sensor film polymer matrix having a blend of conductive carbon black particles is prepared by adding the following materials: 15 grams of a methacryloxypropyl end-blocked silicone polymer, commercially available as GP-478 from Genesee Polymers, Corp. of Flint, Mich., with 9.3 grams of a 7-13% hydromethylsiloxane-87-93% octylmethylsiloxane polymer (HAM 301 commercially available from Gelest, Inc. of Tullytown, Pa.); 0.09 grams of a platinum carbonyl cyclovinylmethylsiloxane catalyst complex (commercially available as SIP 6829 from Gelest). The particles, siloxane polymer precursors, and catalyst are added to a Brabender® mixer for 15 minutes at 30° C. and 80 rpm to form a matrix mixture. The mixture is then applied in a groove over electrodes in a sensor structure. The sensor structure having the matrix mixture applied is then cured for 8 hours at 130° C.

EXAMPLE 2

A single-use sensor film polymer matrix having a blend of conductive carbon black particles can be prepared by adding the following materials: 13.8 grams of a methacryloxypropyl end-blocked silicone polymer, commercially available as GP-478 from Genesee Polymers, Corp. of Flint, Mich., with 10.8 grams of a 7-13% hydromethylsiloxane-87-93% octylmethylsiloxane polymer available as HAM 301; 0.09 grams of a platinum carbonyl cyclovinylmethylsiloxane catalyst complex (commercially available as SIP 6829 from Gelest, Inc. of Tullytown, Pa.). The particles, siloxane polymer precursors, and catalyst are added to a Brabender® mixer for 15 minutes at 30° C. and 80 rpm to form a matrix mixture. The mixture is then applied in a groove over electrodes in a sensor structure. The sensor structure having the matrix mixture applied is then cured for 8 hours at 130° C.

The sensor films prepared in accordance with Examples 1-2 exhibit sensitivity to one or more volatile organic compounds, while further having a sustained increase in resistance after a detection event, thus are particularly advantageous for single-use sensor film applications.

In various aspects, the present disclosure provides a single-use conductometric sensor film that comprises a replaceable sensor film matrix in electrical communication with one or more electrodes of a conductometric sensor probe that detects one or more target analytes comprising volatile organic compounds. When one or more target analytes are substantially absent in the surrounding environment, the matrix exhibits a first baseline resistance. When one or more target analytes are present, the matrix exhibits a second resistance and further undergoes a substantially inelastic deformation to maintain a sustained resistance that is greater than the first baseline resistance. The matrix comprises a crosslinked siloxane polymer and a plurality of conductive particles distributed within the polymer.

In certain aspects, the single-use conductometric sensor film matrix has a first initial volume prior to exposure to one or more target analytes and a second expanded volume after exposure to one or more target analytes resulting in the sustained increase in resistance.

In other aspects, the present disclosure provides methods of detecting one or more volatile organic compound target analytes. For example, in one aspect, such a method includes monitoring an electrical potential of a sensor film matrix comprising a crosslinked siloxane polymer and a plurality of conductive particles. The polymer undergoes a substantially inelastic deformation in the presence of the target analytes, such as described above. The method also comprises detecting the presence of the target analytes by detecting a change in resistance of the sensor film matrix, where the sensor film matrix interacts with the target analytes and undergoes a substantially inelastic deformation. In certain aspects, after the detecting of the presence of analytes, a sustained resistance of the sensor film matrix is relatively high, prohibiting reuse of the sensor film matrix. Thus, in certain aspects, after detecting the analytes, the sensor film is replaced with a new sensor film having the same composition and base resistance of the used sensor film prior to exposure to analytes.

Thus, the sensor film matrices according to the present disclosure have sensor stability and good sensitivity to accurately detect one or more volatile organic compound target analytes, while ensuring the long-term accuracy of the sensor readings of analyte concentration, by necessitating the replacement of a spent sensor film after a detection event, thus improving safety and reducing potential detection errors. The description of the disclosure and examples provided herein is merely exemplary in nature and, thus, variations that do not depart from the gist of the disclosure are intended to be within the scope of the disclosure. Such variations are not to be regarded as a departure from the spirit and scope of the present teachings.

What is claimed is:

1. A single-use conductometric sensor film comprising:
a single-use sensor film matrix in electrical communication with one or more electrodes of a conductometric sensor probe that detects one or more target analytes comprising volatile organic compounds, wherein in the substantial absence of said one or more target analytes, said matrix has an initial volume and exhibits a first baseline resistance and after a detection event occurs in the presence of said one or more target analytes, said matrix has an expanded volume and further undergoes a substantially inelastic deformation after said detection event so that said single-use sensor film matrix is incapable of reverting back to the initial volume and thus is prohibited from reuse after a single detection event, wherein said matrix comprises a crosslinked siloxane polymer that is a reaction of greater than or equal to about 50% of a first siloxane precursor having at least one terminal functional vinyl group and a second siloxane precursor comprising a hydride and a plurality of conductive particles distributed within said cross-linked siloxane polymer.

2. The single-use conductometric sensor film of claim 1, wherein said crosslinked siloxane polymer is formed with said first siloxane precursor comprising a methacrylate group.

3. The single-use conductometric sensor film of claim 1, wherein said first siloxane precursor comprises greater than or equal to about 50 weight % to about 80 weight % of the total amount of the crosslinked siloxane polymer.

4. The single-use conductometric sensor film of claim 1, wherein a ratio of said first siloxane precursor to said second siloxane precursor is about 1:10 to about 1:1 by weight.

5. The single-use conductometric sensor film of claim 1, wherein said crosslinked siloxane polymer is formed by a methacryloxy terminated siloxane precursor having a structure of:

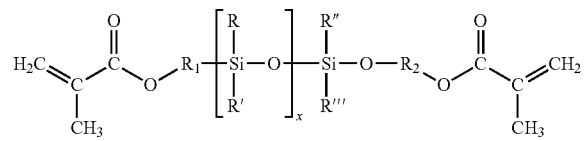

wherein each of R, R', R", and R''' is selected independently and comprises a hydrocarbon side group, $R_1$ and $R_2$ comprise an alkyl group; x ranges from about 65 to 100 and an average number molecular weight is about 650 to about 6,000.

6. The single-use conductometric sensor film of claim 5, wherein R, R', R", and R''' are each selected as $CH_3$, $R_1$ and $R_2$ are each selected as $C_3H_6$, x equals 65 and said average number molecular weight is about 5,000, wherein the structure is represented by:

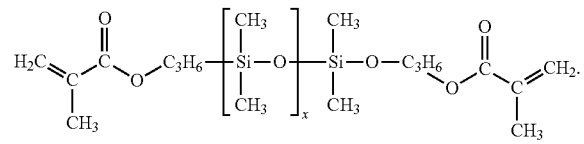

7. The single-use conductometric sensor film of claim 5, wherein each said hydrocarbon side group R, R', R", and R''' is independently selected from the group consisting of: ethyl, propyl, butyl, pentyl, hexyl, heptyl, octyl, nonyl, decyl, phenyl, alkylphenyl, cyclopentyl, phenylpropyl, butylated aryloxypropyl, N-pyrrolidonepropyl, cyanopropyl, benzyltrimethyl ammonium chloride, hydroxyalkyl, and combinations thereof.

8. The single-use conductometric sensor film of claim 1, wherein said conductive particles are selected from the group consisting of: gold, platinum, graphite, carbon black, nickel, conductive metal borides, nitrides and carbides, and mixtures thereof.

9. A single-use conductometric sensor film matrix comprising a crosslinked siloxane polymer and a plurality of conductive particles distributed within said polymer, wherein in the substantial absence of one or more target analytes comprising volatile organic compounds, the sensor film matrix has an initial volume and exhibits a first baseline resistance and in the presence of said one or more target analytes comprising volatile organic compounds the sensor film matrix has an expanded volume and the polymer undergoes a substantially inelastic deformation after a detection event occurs in the presence of said one or more target analytes comprising volatile organic compounds so that the sensor film matrix is incapable of reverting back to the initial volume and thus is prohibited from reuse after said detection event, wherein said crosslinked siloxane polymer is from a reaction of a siloxane precursor comprising a hydride and a methacryloxy terminated siloxane precursor having a structure of:

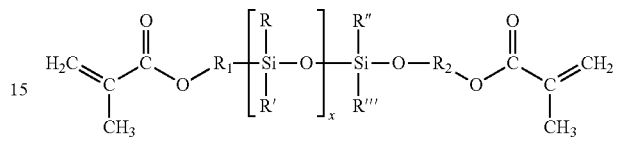

wherein each of R, R', R", and R''' are independently selected from a hydrocarbon side group, $R_1$ and $R_2$ are independently selected from an alkyl group; x ranges from about 65 to about 100 and has an average number molecular weight of about 650 to about 6,000.

10. The single-use conductometric sensor film matrix of claim 9, wherein R, R', R", and R''' are each selected as $CH_3$, $R_1$ and $R_2$ are selected as $C_3H_6$, x equals 65 and said average number molecular weight is about 5,000, wherein the structure is represented by:

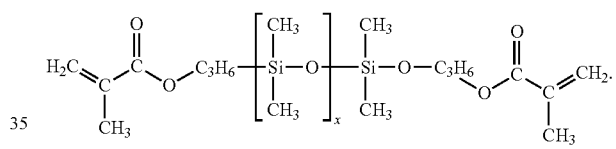

11. The single-use conductometric sensor film matrix of claim 9, wherein said siloxane precursor comprising a hydride comprises 7-13% hydromethylsiloxane and 87-93% octylmethylsiloxane.

12. The single-use conductometric sensor film matrix of claim 9, wherein a ratio of said methacryloxy terminated siloxane precursor to said siloxane precursor comprising a hydride is about 1:10 to about 1:1 by weight.

13. A method of detecting one or more volatile organic compound target analytes comprising:
monitoring an electrical potential of a single-use sensor film matrix having an initial volume and a baseline resistance disposed within a conductometric sensor probe, wherein said single-use sensor film matrix comprises a plurality of conductive particles and a crosslinked siloxane polymer that is a reaction of a siloxane precursor having at least one terminal functional group at greater than or equal to about 50% of the total amount of said crosslinked siloxane polymer;
detecting the presence of the one or more volatile organic compound target analytes in a detection event by detecting a change in resistance from said baseline resistance, wherein during the detection event said single-use sensor film matrix interacts with the one or more volatile organic compound target analytes so as to undergo a substantially inelastic deformation to form a spent single-use sensor film matrix having a second expanded volume incapable of reverting back to said initial volume, thereby prohibiting reuse of said single-use sensor film matrix; and removing said spent single-use sensor film matrix from said conductometric sensor probe after said detection event.

14. The method of claim 13, wherein said baseline resistance exhibited by said sensor film matrix prior to said detecting of the one or more volatile organic compound target analytes in said detection event at ambient temperature and pressure conditions is less than or equal to about 100 Ohm.

15. A method of detecting one or more volatile organic compound target analytes comprising:
monitoring an electrical potential of a single-use sensor film matrix having an initial volume and a baseline resistance disposed within a conductometric sensor probe, wherein said single-use sensor film matrix comprises a plurality of conductive particles and a crosslinked siloxane polymer that is a reaction of a siloxane precursor comprising a hydride and a methacryloxy terminated siloxane precursor having a structure of:

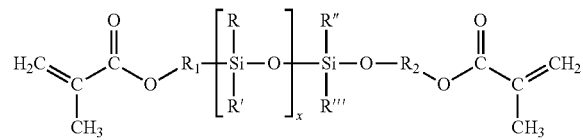

wherein each of R, R', R", and R''' is selected independently and comprises a hydrocarbon side group, $R_1$ and $R_2$ each comprise an alkyl group; x ranges from about 65 to about 100 and an average number molecular weight is about 650 to about 6,000;
detecting the presence of the one or more volatile organic compound target analytes in a detection event by detecting a change in resistance from the baseline resistance, wherein during said detection event said single-use sensor film matrix interacts with the one or more volatile organic compound target analytes so as to undergo a substantially inelastic deformation to form a spent single-use sensor film matrix having a second expanded volume incapable of reverting back to said initial volume, thereby prohibiting reuse of said single-use sensor film matrix; and
removing said spent single-use sensor film matrix from said conductometric sensor probe after said detection event.

16. The method of claim 15, wherein a ratio of said methacryloxy terminated siloxane precursor to said siloxane precursor comprising a hydride is about 1:10 to about 1:1 by weight.

17. The method of claim 15, wherein said hydride comprises 7-13% hydromethylsiloxane and 87-93% octylmethylsiloxane.

* * * * *